US00PP25697P3

(12) United States Plant Patent
Clark et al.

(10) Patent No.: US PP25,697 P3
(45) Date of Patent: Jul. 14, 2015

(54) GRAPE PLANT NAMED 'HOPE'

(50) Latin Name: ***Vitis labrusca* L.×*Vitis vinifera* L.**
Varietal Denomination: Hope

(71) Applicant: THE BOARD OF TRUSTEES OF THE UNIVERSITY OF ARKANSAS, Little Rock, AR (US)

(72) Inventors: John Reuben Clark, Fayetteville, AR (US); James N. Moore, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 191 days.

(21) Appl. No.: 13/987,494

(22) Filed: Jul. 31, 2013

(65) Prior Publication Data

US 2015/0040276 P1 Feb. 5, 2015

(51) Int. Cl.
*A01H 5/00* (2006.01)

(52) U.S. Cl.
USPC ..... Plt./207

(58) Field of Classification Search
USPC ..... Plt./207
See application file for complete search history.

(56) References Cited

U.S. PATENT DOCUMENTS

PP13,309 P2 12/2002 Clark
2012/0297511 P1 11/2012 Clark et al.

OTHER PUBLICATIONS

Clark, J.R. et al., "'Faith', 'Gratitude', 'Hope', and 'Joy' Seedless Table Grapes," (2013) HortScience 48(7):913-919.
Clark, J.R. et al., "'Osage' Thornless Blackberry and 'Hope', 'Faith', 'Joy', and 'Gratitude' Table Grapes," (2013) SR-ASHS Annual conference HortScience 48(9) (Supplement)—2013 SR-ASHS Annual Meeting, p. S33.
U.S. Appl. No. 13/987,496, filed Jul. 31, 2013.
U.S. Appl. No. 13/987,497, filed Jul. 31, 2013.
U.S. Appl. No. 13/987,501, filed Jul. 31, 2013.

*Primary Examiner* — Annette Para
(74) *Attorney, Agent, or Firm* — Andrus Intellectual Property Law, LLP

(57) ABSTRACT

Description and specifications of a new and distinct grapevine cultivar named 'Hope' which originated from a hand-pollinated cross of A-1562 (non-patented, non-released breeding genotype)×A-1704 (non-patented, non-released breeding genotype). This new grapevine cultivar can be distinguished by its very tight large clusters, fruity flavor, high yields, medium vigor, and healthy plant.

3 Drawing Sheets

Latin name: *Vitis labrusca* L.×*Vitis vinifera* L.
Varietal denomination: 'Hope'.

BACKGROUND

The new and distinct cultivar of grape named 'Hope' is described herein. The new cultivar originated from a hand-pollinated cross of A-1562 (female parent) and A-1704 (male parent) made in 1985. The seedlings fruited in the summer of 1986 in a vineyard near Clarksville, Ark. and one was selected for its seedless, green berries with good flavor. The fruit grows in tight clusters, the vines have medium vigor and the plants are very productive and healthy.

SUMMARY OF THE INVENTION

The new and distinct cultivar of grapevine originated from a hand-pollinated cross of A-1562 (non-patented, non-released breeding genotype; female parent)×A-1704 (non-patented, non-released breeding genotype; male parent) made in 1985 near Clarksville, Ark. The instant cultivar is a hybrid of *Vitis labrusca* L. and *Vitis vinifera* L. The seeds resulting from this controlled hybridization were germinated in a greenhouse during the winter of 1985-86. Resulting seedlings were planted in the spring of 1986 in a vineyard near Clarksville, Ark. The seedlings fruited in the summer of 1986 and one seedling, designated Arkansas Selection 2053, was selected for its seedless, green berries with a fruity flavor, tight clusters, medium vigor, and productive and healthy plant.

During late 1986 and early 1987, the original plant selection was propagated asexually at the above-noted location, by rooting hardwood cuttings and a test planting of three vines was established. In all propagations hardwood cuttings were used and the instant cultivar rooted readily from hardwood cuttings. All propagules (resulting plants) of the instant cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have medium vigor, with a procumbent growth habit characteristic of *V. labrusca*. It has produced well as own-rooted plants in all testing and has not been evaluated on any rootstocks. Hardiness of the vines has been very good, with no winter injury to the vines to 5° F. in the most severe winters at the Arkansas test site.

The new cultivar is moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopora viticola* Berl. & Tomi.), and anthrancnose (*Elsinoe ampelina* (d. By.) Sher), but susceptible to black rot (*Guignardia bidwellii* (Ell.) V. & R.). Fungal diseases can be controlled by the use of available fungicides.

The new cultivar ripens its fruit in the mid- to late-season, average August 18. The fruit is green in color at early maturity. It is evenly colored within the cluster. The fruit shape is oval. Fruit skins are moderately thick and adhere to the flesh (has a non-slipskin texture). The berries are medium-small (ca. 3.4 g). The flavor is fruity, and of a *V. labrusca* character. Solids concentration of the juice at fruit maturity averages 20% with medium acidity. The fruit is of the stenospermocarpic type of seedlessness and can contain 1-2 small, soft vestigial seed traces that are not noticeable when eaten. Fruit clusters, borne usually one to two per shoot, are large, and tightly filled with an average weight of 310 g. The fruit clusters are good sized and vines are very productive.

The new cultivar has been named the 'Hope' cultivar.

BRIEF DESCRIPTION OF THE PHOTOGRAPHS

The accompanying photographs show typical specimens of the new variety at 19 years of age in color as nearly true as it is reasonably possible to make in a color illustration of this character.

DETAILED DESCRIPTION OF THE NEW CULTIVAR

Figure 1:
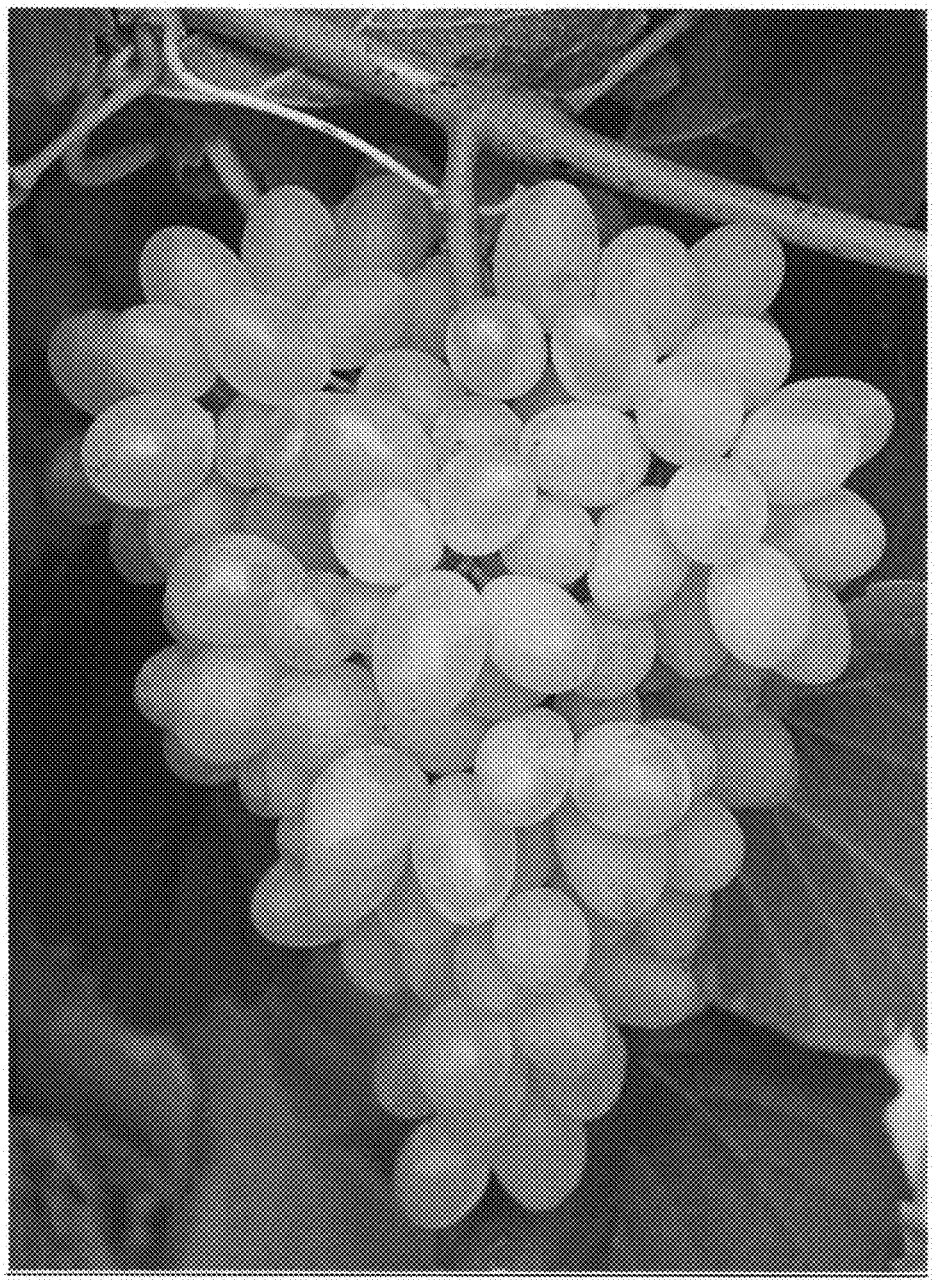
FIG. 1 is a photograph showing typical specimens of the fruit.
Figure 2:
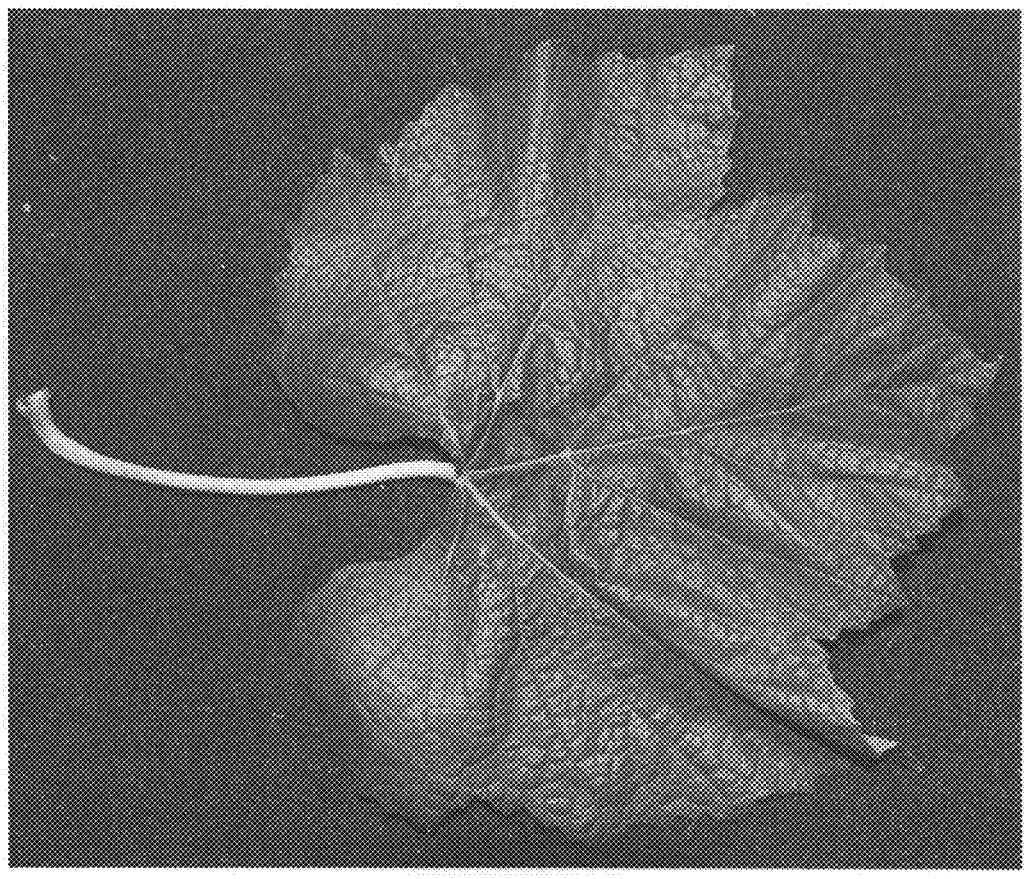
FIG. 2 is a photograph showing the leaf adaxial view.
Figure 3:
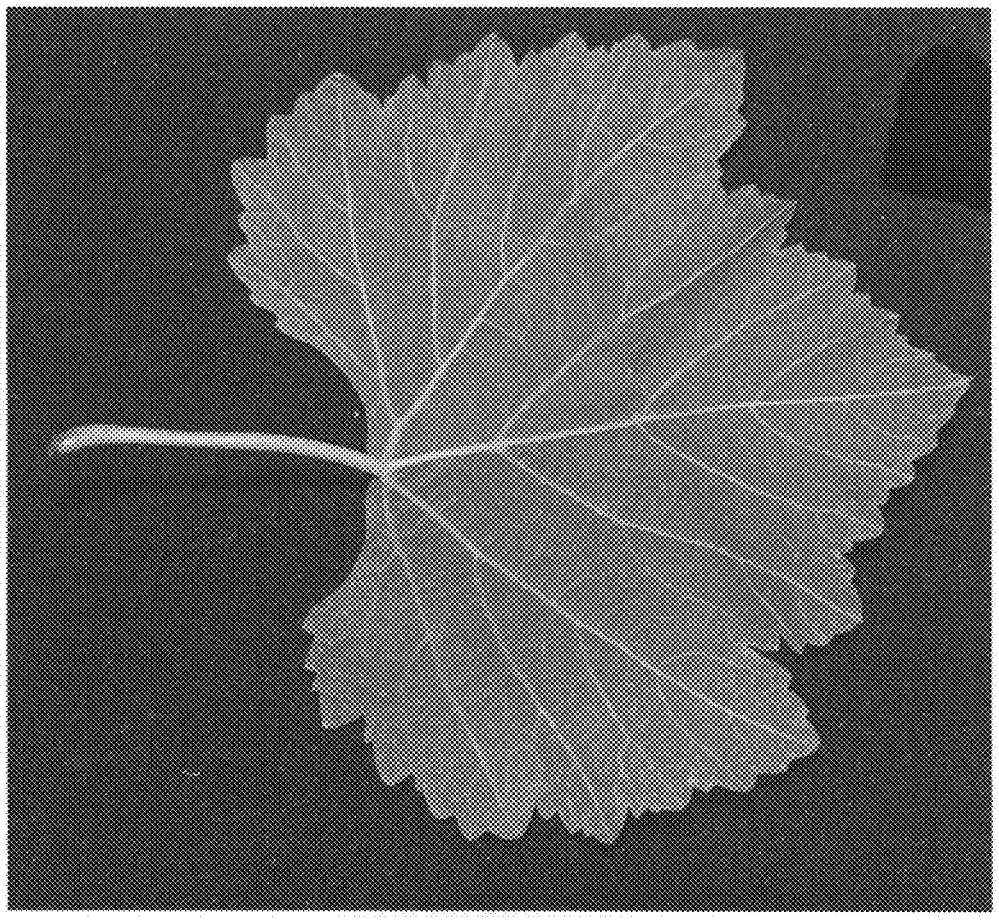
FIG. 3 is a photograph showing the leaf abaxial view.

'Hope' differs from its female parent A-1562 in that it has tighter clusters, is seedless, and green instead of blue/black fruit color. 'Hope' differs from it male parent A-1704 as this parent has much smaller clusters.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. The data collection was from vines that were 15 years old.

Vine:

*Size*.—Medium.

*Growth*.—Moderately vigorous.

*Density of foliage*.—Medium.

*Productivity*.—High yielding.

*Rootstock*.—None; vines tested were own-rooted vines.

*Cold hardiness*.—Hardy to 5° C. (−15° C.); possibly more hardy as this was the coldest temperature experienced at the test site.

*Shoots* (*current-season canes*).—Color of shoots on the side exposed to direct sunlight — Yellow-Green Group (146C). Color on the side shaded from the sun Yellow-Green Group (146C). Anthocyanin not present. Shoot attitude is procumbent.

*Canes* (*mature measured in winter*).—Color of mature cane: base mostly Greyed-Orange Group (165A) and some 165B; midpoint mostly Greyed-Orange Group (165A and some 165B); terminal Greyed-Orange Group (165A and some 165B); anthocyanin not observed on mature canes at base, midpoint, or terminal. Length average 2 m with range of 1.5 to 3.1 m. Diameter of mature cane: base 1.1 cm, midpoint 0.8 cm, terminal 0.6 cm. Internode length: base 4.2 cm, midpoint 10.1 cm, terminal 5.1 cm. Lenticels present on mature canes at medium density and small (less than 0.5 mm in diameter). Canes mature to tips in the fall.

Trunk:

*Shape*.—Slender.

*Trunk straps*.—Long, split.

*Surface texture*.—Shaggy.

*Inner bark color*.—Greyed-orange group, 166-A.

*Outer bark color*.—Grey group, 201-A.

Foliage:

*Leaves*.—Leaves simple and alternate; shape palmate; number of lobes 3; petiole sinus shape half open; venation palmate-pinnate; margin serrated with shape of teeth convex and teeth medium in size. The leaf surface has a smooth/waxy texture. Color of mature leaves: base abaxial — Yellow-Green Group (146B); base adaxial — Yellow-Green Group (146A); midpoint abaxial — Yellow-Green Group (146A); midpoint adaxial — Yellow-Green Group (146A); terminal abaxial — Yellow-Green Group (146A); terminal adaxial — Yellow-Green Group (146A). Anthocyanin present on terminal adaxial surface in between leaf veins. Color of young leaves: base abaxial — Yellow-Green Group (146C); base adaxial — Yellow-Green Group (146B); midpoint abaxial — Yellow-Green Group (146C); midpoint adaxial — Yellow-Green Group (146B); terminal abaxial — Yellow-Green Group (145D); terminal adaxial — Yellow-Green Group (145C).

*Petioles*.—Color on young leaves — Yellow-Green Group (146C). Color of mature petioles — Yellow-Green Group (146C). Petiole anthocyanin present on young leaves on the side exposed to sunlight on upper terminal leaves. Petiole anthocyanin absent on mature leaves. Sinus of mature leaf is 2.8 cm deep and 5.2 cm at widest point. Mature leaves have sparse pubescence on midrib. Young leaves have light pubescence between ribs on abaxial surface, with a medium amount on midrib, main veins, and secondary veins.

*Tendrils*.—Found beginning on $4^{th}$ and $5^{th}$ node, opposite. Length — 17.2 cm. Texture — smooth and usually forked and curled on distal end. Color of mature tendril — Greyed-Orange Group 165A.

*Buds*.—Average number of buds on a current, single-season cane 27.3. Dormant bud (compound bud or eye) width 5.9 mm; shape triangular. Color — Greyed-Orange Group (165A). Texture — smooth.

Disease resistance: Moderately resistant to powdery mildew, and downy mildew; susceptible to black rot. Other disease or pest susceptibilities not known.

Flowers:

*Sex*.—Hermaphrodite.

*Date of bloom*.—May 6 (first); May 10 (full). Flowers per cluster — 950.

*Stamens*.—Number: 5 to 6 and erect. Color: Filament — White Group (155B); Anther — Yellow Group (12B).

*Pistil*.—Number: 1. Length: 2.5 mm. Color: Yellow-Green Group (144A).

*Pollen*.—Color: Yellow-Green Group (1A), normal and fertile.

*Petal*.—Cap of 5 fused petals in tubular shape. Color: Yellow-Green Group (144B).

*Sepal*.—5 sepals in Yellow-Green Group (144B).

Fruit:

*Maturity*.—Mid to late in the season; average first ripe date 18 August.

Berry.—Shape — Oval. Color — Yellow-Green Group (152D). Size — Diameter at equator: 1.5 cm. Diameter at base: 1.1 cm. Diameter at apex: 1.1 cm. Length: 2.4 cm. Weight: 3.4 g; range 3.0 to 3.9 g. Texture — Non-slipskin. Skin thickness — Medium. Seeds — Seedless. Brush length — 5.04 mm. Flavor — fruity flavor.

*Juice*.—pH — 3.6. Titratable acidity — 3.9 g/L tartaric acid. Soluble solids — 20%.

*Cluster*.—Weight — 236-329 g, mean=310 g. Length — 16.5 cm. Width — 10.2 cm. Berries per cluster — 47-283, mean=162. Cluster per vine — 112. Clusters per shoot — 1 to 2. Peduncle length — 1.53 cm. Pedicle: Length — 1.21 cm. Diameter — 0.12 cm. Color — Yellow-Green Group (151A).

Use: Fresh consumption as a table grape is the primary use; local market sales are the primary use. No processing evaluations done.

The cultivar: The most distinctive features of the cultivar are its very tight large clusters, fruity flavor, high yields, medium vigor, and healthy plant.

We claim:

1. A new and distinct cultivar of grape plant named 'Hope' substantially as illustrated and described.

* * * * *